US00PP33271P2

(12) United States Plant Patent
Shefelbine

(10) Patent No.: US PP33,271 P2
(45) Date of Patent: Jul. 20, 2021

(54) APPLE TREE NAMED 'DS 102'

(50) Latin Name: *Malus domestica*
Varietal Denomination: DS 102

(71) Applicant: Doug Shefelbine, Holmen, WI (US)

(72) Inventor: Doug Shefelbine, Holmen, WI (US)

(73) Assignee: Doug Shefelbine, Holmen, WI (US)

( * ) Notice: Subject to any disclaimer, the term of this patent is extended or adjusted under 35 U.S.C. 154(b) by 0 days.

(21) Appl. No.: 16/873,839

(22) Filed: Jul. 21, 2020

(51) Int. Cl.
*A01H 5/08* (2018.01)
*A01H 6/74* (2018.01)

(52) U.S. Cl.
USPC ..... Plt./172
CPC ..... *A01H 6/7418* (2018.05)

(58) Field of Classification Search
USPC ..... Plt./161, 172
CPC ..... A01H 5/0875
See application file for complete search history.

*Primary Examiner* — Kent L Bell
(74) *Attorney, Agent, or Firm* — Lee & Hayes, P.C.

(57) ABSTRACT

A new and distinctive seedling of *Malus domestica* apple that is distinguished by its complete uniform color pattern, unique eating equality, and long storage life for a mid-season apple.

5 Drawing Sheets

Latin name: *Malus domestica.*
Varietal denomination: 'DS 102'.

BACKGROUND

The present invention relates to a novel and distinct variety of apple tree which has been denominated varietally as 'DS 102'. More specifically, the present invention relates to a novel mid-season apple tree that is considered hardy for north-central Washington state, moderate on the low side in vigor, and considered spur that will tip bear. The novel apple tree produces uniform, golden-colored fruit with non-protruding lenticels that is not russeted, considered medium-large, and has a 9-month storage life. The flesh of the fruit is snappy, crisp, juicy, and melting.

ORIGIN AND ASEXUAL REPRODUCTION

It has long been recognized that important factors contributing to the success of a new variety of apple tree bearing fresh market fruit are the characteristics of both its growth and fruit. Other significant factors affecting the commercial viability of a new variety of apple include storage characteristics, which are reflected by pomological traits. The new variety of apple tree described herein was derived by the following methodology.

In 1994, seeds from open pollinated 'Honeycrisp' (U.S. Plant Pat. No. 7,197P) fruit were collected. As such, 'DS 102' is most closely related to the 'Honeycrisp'. In 1995, those seeds were planted in an orchard located in Holman, Wis., USDA Hardiness Zone 4A. In 2005, 'DS 102' was selected from the surviving seedlings. In August 2007, second-generation trees were budded on M26 rootstock (unpatented) and in spring 2009, planted in Brewster, Wash., USDA Hardiness Zone 6B. Fruit from the second-generation trees were studied and observed from 2011 through 2019, and it appears that all characteristics of the subsequent trees remain true to that seen in the original first-generation "mother" tree.

SUMMARY OF NEW VARIETY

The 'DS 102' apple tree is a new and distinctive seedling of *Malus domestica* and is characterized as novel by its complete uniform color pattern, its unique quality being exceptionally firm, crisp, and sweet, and its long storage life. 'DS 102' is further characterized from its distinctive traits from its parent variety and closest known cultivar, 'Honeycrisp'. The leaf of 'DS 102' is broadly acute and slightly larger in length and width than the 'Honeycrisp', whose leaves are ovate. The peduncle length and width of 'DS 102' is significantly larger than that of the 'Honeycrisp', and 'DS 102' contains a unique king bloom which exhibits a peduncle which is shorter than that of the side bloom. 'DS 102' presents a golden colored skin while the 'Honeycrisp' is bi-colored. The skin of such fruit is not russeted, is smooth and uniform colored with non-protruding lenticels, and does not bruise easily during handling.

BRIEF DESCRIPTION OF DRAWINGS

The accompanying drawings are color photographs of the present variety, 11 year-old trees grown in Brewster, Wash. 98812, USDA Hardiness Zone 6A.

NOT A COMMERCIAL WARRANTY

Figure 1:
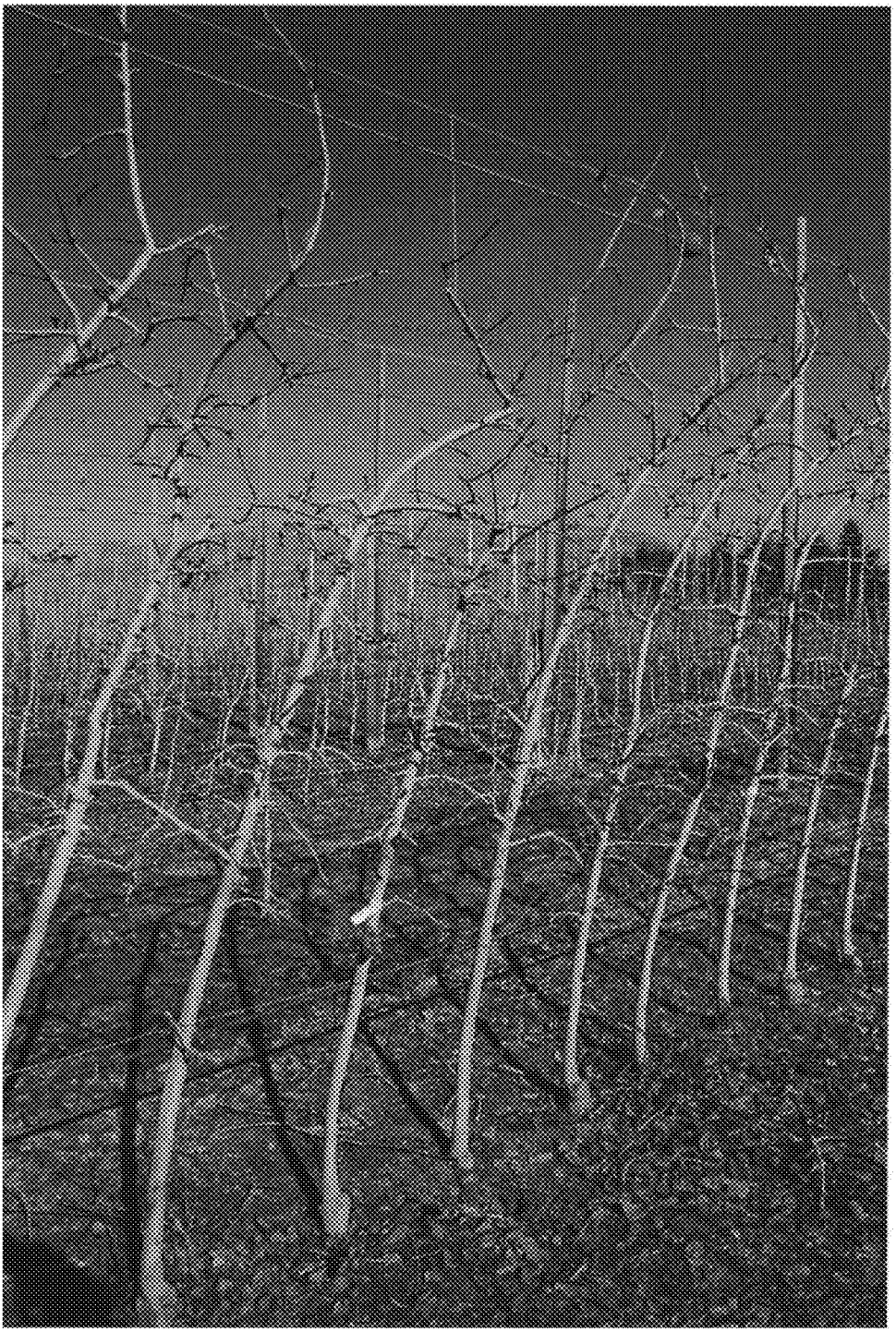
FIG. 1 depicts a dormant second-generation 'DS 102' tree.
Figure 2:
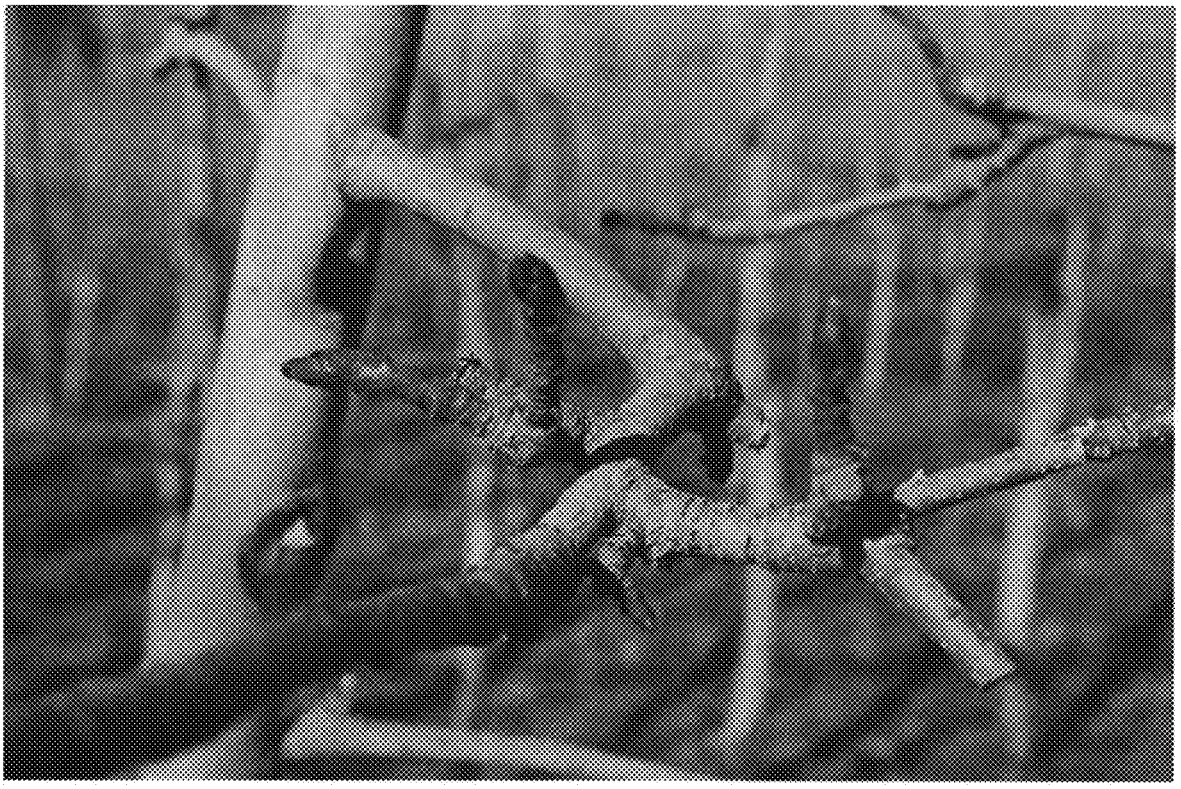
FIG. 2 depicts second-generation 'DS 102' spur development.
Figure 3:
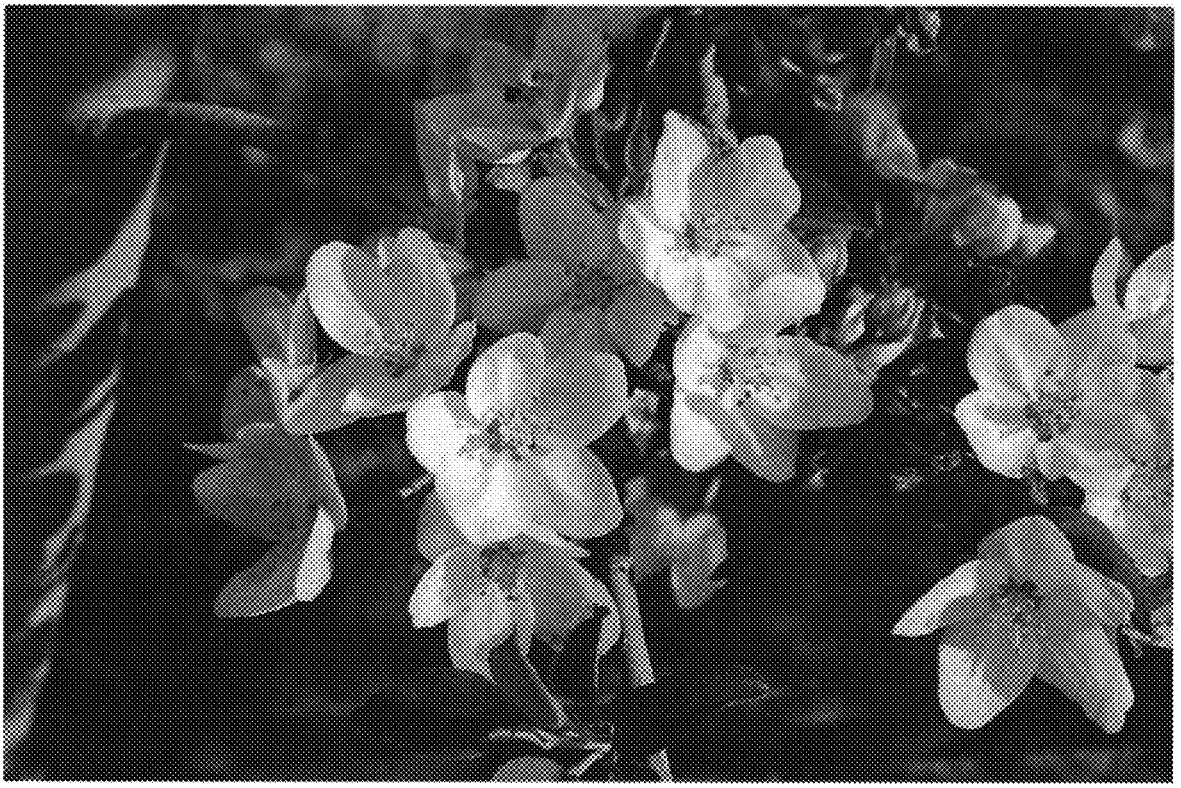
FIG. 3 depicts a second-generation 'DS 102' at near full bloom.
Figure 4:
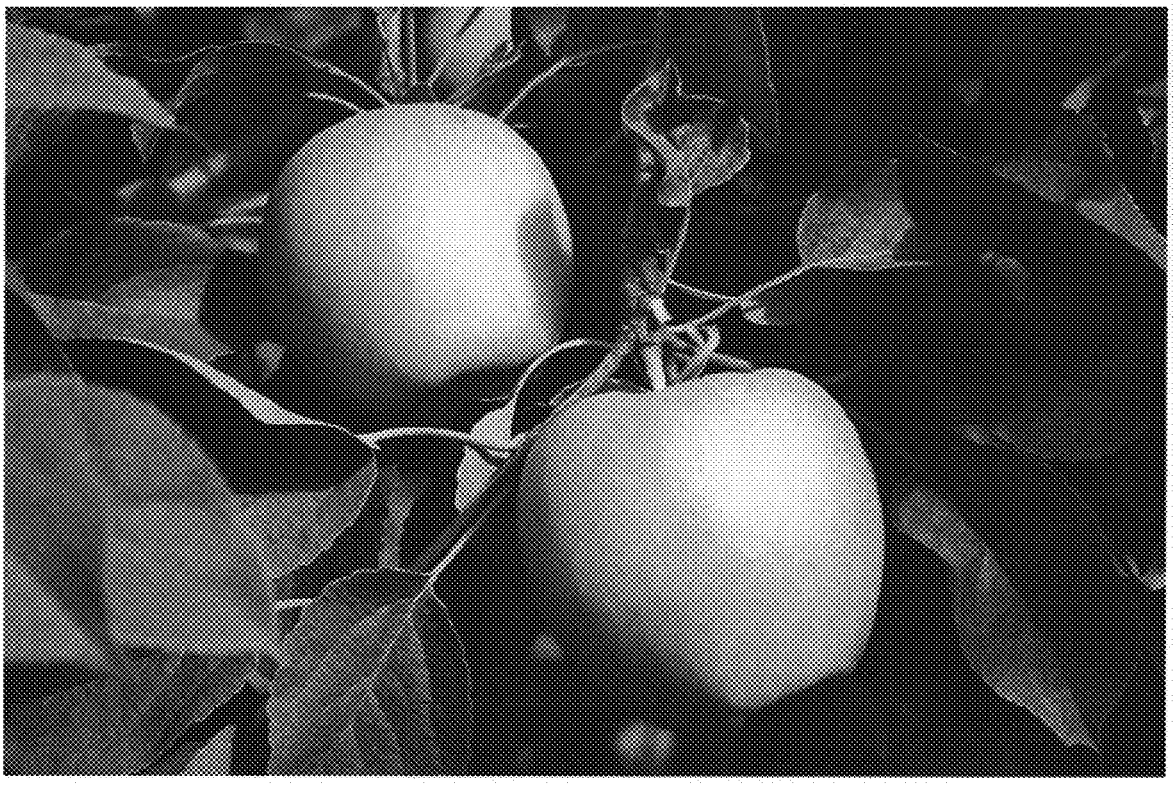
FIG. 4 depicts a fruiting limb of a second-generation 'DS 102' pre-harvest.
Figure 5:
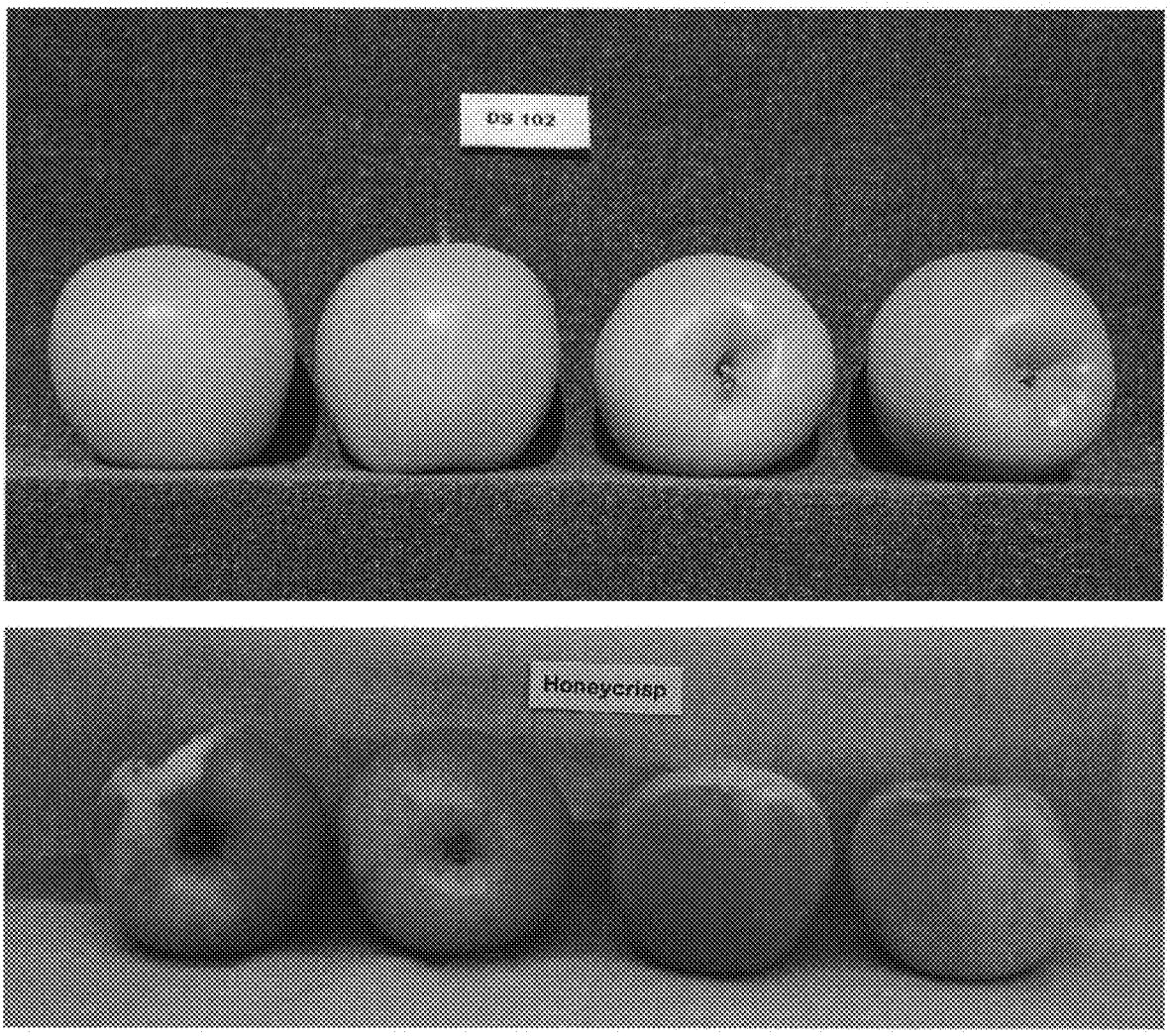
FIG. 5 illustrates four positions of harvest-mature 'DS 102' fruit in comparison with a Honeycrisp.

The following detailed description has been prepared to solely comply with the provisions of 35 U.S.C. § 112, and does not constitute a commercial warranty, (either expressed or implied), that the present variety will, in the future, display the botanical, pomological or other characteristics as set forth herein. Therefore, this disclosure may not be relied upon to support any future legal claims, including but not limited to breach of warranty of merchantability, or fitness for any particular purpose, which is directed, in whole, or in part, to the present variety.

DETAILED DESCRIPTION

Referring more specifically to the pomological and botanical details of this new and distinct variety of apple tree, the following has been observed from second-generation, 11 year-old trees grown in Brewster, Wash. 98812, USDA Hardiness Zone 6A. All color references are from The R.H.S. Colour Chart by The Royal Horticulture Society.

Tree:

*Tree as trained*.—Wire supported slender spindle.

*Tree type*.—Spur and tip bearer.

*Tree vigor*.—Considered moderate on the low side.

*Tree shape*.—Upright and spreading.

*Tree height*.—About 10 feet.

*Tree width*.—About 3 feet.

*Hardiness*.—Considered hardy for north-central Washington.

*Fruit productivity*.—Considered low to moderate (will alternate bear if conditions are right) with about 45 bins per acre.

Trunk:

*Trunk diameter*.—About 4.0 centimeters when measured at a height of about 30 centimeters above the ground.

*Bark texture*.—Generally smooth.

*Bark color*.—From the Greyed-Orange group (RHS 163A).

*Trunk lenticels*.—About 11 per 9 centimeters of growth.

*Trunk lenticel width*.—From about 1.0 millimeters to about 1.2 millimeters with an average of about 1.1 millimeters.

*Trunk lenticel length*.—From about 3.2 millimeters to about 5.4 millimeters with an average of about 4.2 millimeters.

*Trunk lenticel color*.—From the Brown group (RHS N200B).

*Trunk lenticel shape*.—Generally flat.

Branches:

Scaffold branches:

*Scaffold branch diameter*.—From about 9.8 millimeters to about 14.5 millimeters with an average of about 12.3 millimeters as measured at 10 centimeters from the trunk.

*Scaffold branch length*.—Ranging from about 26.6 centimeters to about 48.0 centimeters with an average of about 34.4 centimeters.

*Scaffold branch color*.—From the Greyed-Orange group (RHS 163A).

*Scaffold branch texture*.—Generally smooth.

*Scaffold branch angle*.—As trained, about 60 degrees to about 90 degrees from vertical.

*Scaffold branch lenticels*.—About 10 lenticels per 9 square centimeters.

*Scaffold branch lenticel shape*.—Generally round.

*Scaffold branch lenticel diameter*.—From about 0.8 millimeters to about 1.9 millimeters with an average of about 1.5 millimeters.

*Scaffold branch lenticel color*.—Outer margin from the Yellow-White group (RHS 158A). Center from the Greyed-Orange group (RHS 167A).

*Two-year-old branch length*.—Ranging from about 26.6 centimeters to about 48.0 centimeters with an average of about 48.0 centimeters.

Two-year-old fruiting branches:

*Two-year-old branch diameter*.—From about 3.7 millimeters to about 6.3 millimeters with an average of about 4.7 millimeters.

*Two-year-old branch texture*.—Generally smooth.

*Two-year-old branch pubescence*.—None.

*Two-year-old branch color*.—From the Greyed-Orange group (RHS 163A).

*Two-year-old branch lenticel numbers*.—Present and averaging about 14 per running centimeter.

*Two-year-old branch lenticel shape*.—Generally round.

*Two-year-old branch lenticel diameter*.—Ranging from about 1.0 millimeters to about 1.3 millimeters.

*Two-year-old branch lenticel color*.—From the Yellow-White group (RHS 158A).

*Two-year-old branch internode length*.—Ranging from about 27.9 millimeters to about 50.6 millimeters with an average of about 36.4 millimeters.

Two-year-old branch spur development:

*Two-year-old branch spur length*.—Ranging from about 8.3 millimeters to about 14.1 millimeters with an average of about 10.3 millimeters.

*Two-year-old branch spur width*.—About 4.7 millimeters.

*Two-year-old branch bud shape*.—More globose than elliptical.

*Two-year-old branch spur bud length*.—Ranging from about 5.5 millimeters to about 9.6 millimeters with an average of about 7.3 millimeters.

*Two-year-old branch spur bud diameter*.—Ranging from about 4.0 millimeters to about 5.3 millimeters with an average of about 4.6 millimeters.

*Two-year-old branch bud scale color*.—From the Greyed-Purple group (RHS 183A).

*Two-year-old branch spur pubescence*.—Wanting to very little on the tips.

*Two-year-old branch spur pubescence color*.—From the White group (RHS 155D).

*Two-year-old branch crotch angle*.—From about 30 degrees to about 50 degrees.

2019 branches:

2019 *branch texture*.—Generally smooth.

2019 *branch length*.—Ranging from about 26.5 centimeters to about 40.8 centimeters with an average of about 34.4 centimeters.

2019 *branch diameter at midpoint*.—Ranging from about 3.2 millimeters to about 5.9 millimeters with an average of about 4.7 millimeters.

2019 *branch pubescence*.—Wanting.

2019 *branch pubescence color*.—None.

2019 *branch color*.—From the Greyed-Purple group (RHS 183A).

2019 *branch lenticels*.—Present and averaging about 13 per running centimeter.

2019 *branch lenticel shape*.—Generally round.

2019 *branch lenticel diameter*.—Ranging from about 0.05 millimeters to about 0.1 millimeters.

2019 *branch lenticel color*.—From the White group (RHS N155D).

2019 *branch Internode length*.—Ranging from about 27.9 millimeters to about 50.6 millimeters with an average of about 36.4 millimeters.

Bloom (flowers):

*First bloom date*.—Apr. 19, 2020.

*Full bloom date*.—Apr. 24, 2020.

*Number of blossoms per bud*.—About 6 blossoms.

*Bud size*.—Considered medium-large.

*Bud shape*.—More globose than elliptical.

*Bud length*.—From about 5.5 millimeters to about 9.6 millimeters with an average of about 7.3 millimeters.

*Bud diameter*.—Ranging from about 4.0 millimeters to about 5.3 millimeters with an average of about 4.6 millimeters.

*Blossom diameter when fully open*.—Ranging from about 4.8 centimeters to about 6.2 centimeters with an average of about 5.3 centimeters.

*Blossom depth*.—Ranging from about 11.8 millimeters to about 14.7 millimeters.

*Petal count*.—About 5 petals per blossom.

*Petal shape*.—Mostly deltoid, occasionally oval.

*Petal tip shape*.—Obtuse.

*Petal base shape*.—Rounded.

*Petal width*.—Ranging from about 15.5 millimeters to about 18.7 millimeters with an average of about 16.6 millimeters.

*Petal length*.—From about 20.0 millimeters to about 24.2 millimeters with an average of about 22.3 millimeters.

*Petal margin*.—Smooth.

*Unopened petal color*.—About 80% area from the Red-Purple group (RHS 64B). About 20% area from the Red-Purple group (RHS 63C).

*Opened petal color*.—About 40-80% surface area from the Red-Purple group (RHS 64D). About 20-60% surface area from the White group (RHS N155B).

*Stamen number*.—Ranging from about 18 to about 21 with an average of about 19.

*Stamen filament length*.—Ranging from about 4.9 millimeters to about 9.5 millimeters with an average of about 7.1 millimeters.

*Stamen filament color*.—From the White group (RHS 155C).

*Stamen anthers shape*.—Kidney.

*Stamen anthers length*.—Ranging from about 1.3 millimeters to about 2.0 millimeters with an average of about 1.7 millimeters.

*Stamen athers width*.—From about 1.4 millimeters to about 1.5 millimeters.

*Stamen anthers color*.—From the White group (RHS 155C).

*Stamen anthers mature pollen quantity*.—Moderate.

*Stamen anthers pollen color*.—From the Greyed-Orange group (RHS 165A).

*Pistil style*.—5 in number.

*Pistil length*.—From about 10.1 millimeters to about 12.1 millimeters with an average of about 11.1 millimeters. Style numbers are fused from the base ranging from about 3.6 millimeters to about 5.9 millimeters with an average of about 4.8 millimeters.

*Pistil color*.—From the Yellow-Green group (RHS 145B). Fused area from the White group (RHS 155A).

*Pubescence*.—From the fused area only. About 100% coverage.

*Pubescence color*.—From the White group (RHS 155C).

*Stigma number*.—About 5 per blossom.

*Stigma shape*.—Club.

*Stigma color*.—From the Greyed-Yellow group (RHS 161A).

*Sepal number*.—About 5.

*Sepal shape*.—Lanceolate.

*Sepal shape at tip*.—Narrowly acute.

*Sepal shape at base*.—Flat (truncate).

*Sepal length*.—Ranging from about 5.1 millimeters to about 8.6 millimeters with an average of about 7.5 millimeters.

*Sepal width*.—Ranging from about 3.0 millimeters to about 5.6 millimeters with an average of about 4.0 millimeters.

*Sepal margin*.—Smooth.

*Sepal color*.—Basal end from the Yellow-Green group (RHS 152B). Tip highlights from the Greyed-Purple group (RHS 183B).

*Sepal pubescence*.—Moderate in density over about 100% of both upper and lower surfaces.

*Septal pubescence color*.—From the White group (RHS 155C).

*Peduncle length, king bloom*.—Ranging from about 9.8 millimeters to about 17.6 millimeters with an average of about 13.0 millimeters.

*Peduncle length, side bloom*.—Ranging from about 26.1 millimeters to about 30.4 millimeters with an average of about 28.1 millimeters.

*Peduncle diameter at midpoint, king bloom*.—Ranging from about 1.3 millimeters to about 1.6 millimeters with an average of about 1.5 millimeters.

*Peduncle diameter at midpoint, side bloom*.—Ranging from about 1.1 millimeters to about 1.5 millimeters with an average of about 1.3 millimeters.

*Peduncle color*.—Exposed side from the Red group (RHS 53A). Non-exposed side from the Green group (RHS 138B).

*Peduncle pubescence*.—None.

*Thalamus depth*.—Ranging from about 1.7 millimeters to about 2.6 millimeters with an average of about 2.1 millimeters.

*Thalamus diameter*.—Ranging from about 2.4 millimeters to about 3.2 millimeters with an average of about 2.8 millimeters.

*Thalamus color*.—From the Red group (RHS 53A).

*Thalamus nectary color*.—From the Yellow-Green group (RHS 146B).

*Thalamus pubescence*.—Moderate in density over about 100% of surface area.

*Thalamus pubescence color*.—From the White group (RHS 155C).

Leaves:

*Shape*.—Broadly acute.

*Tip shape*.—Mostly acuminate, some cuspidate.

*Base shape*.—Rounded.

*Length*.—Ranging from about 9.9 centimeters to about 11.3 centimeters with an average of about 10.4 centimeters.

*Width*.—Ranging from about 6.9 centimeters to about 8.8 centimeters with an average of about 7.6 centimeters.

*Margin*.—Mostly serrate with an occasional bi-serrate.
*Upper texture*.—Generally smooth, leathery, and moderate sheen.
*Upper color*.—From the Green group (RHS 139A).
*Lower texture*.—Veins protruding, with about 100% moderate density pubescence.
*Lower pubescence color*.—From the Green-White group (RHS 157D).
*Upper blade color*.—From the Green group (RHS 139A).
*Lower blade color*.—From the Yellow-Green group (RHS 147B).
*Mid vein*.—Protrudes below the lower.
*Mid vein diameter at midpoint*.—Ranging from about 0.8 millimeters to about 1.2 millimeters with an average of about 1.1 millimeters.
*Mid vein color*.—From the Green-White group (RHS 157B).
*Mid vein pubescence*.—Lite density over about 100% of surface area.
*Mid vein pubescence color*.—From the Green-White group (RHS 157D).
*Petiole length*.—Ranging from about 3.0 centimeters to about 4.8 centimeters with an average of about 3.6 centimeters.
*Petiole diameter at midpoint*.—Ranging from about 1.5 millimeters to about 1.8 millimeters with an average of about 1.6 millimeters.
*Petiole upper surface groove*.—Runs full length and ranges from about 0.7 millimeters to about 0.9 millimeters wide and about 0.5 millimeters deep.
*Petiole color*.—From the Green-White group (RHS 157B) (about 5-10% of petiole length).
*Petiole pubescence*.—Lite density over about 100% of surface area.
*Petiole pubescence color*.—From the Green-White group (RHS 157D).
*Petiole attitude*.—Generally flat.
*Stipules*.—Occasionally present and ranging from 0 to 2 per petiole, mostly 0.
*Stipules shape*.—Generally lanceolate.
*Stipules length*.—Ranging from about 5.8 millimeters to about 9.8 millimeters with an average of about 7.3 millimeters.
*Stipules width*.—Ranging from about 0.6 millimeters to about 1.0 millimeters with an average of about 0.7 millimeters.
*Stipules color*.—From the Yellow-Green group (RHS 157D).
*Stipules pubescence*.—None.

Fruit:

*Form*.—Considered Round-Conical.
*Ribs*.—Present in most fruit.
*Ribs number*.—Ranging from 0 to 4 with an average of about 2.
*Weight*.—Ranging from about 151 grams to about 280 grams with an average of about 185 grams.
*Equatorial diameter*.—Ranging from about 7.5 centimeters to about 8.4 centimeters with an average of about 8.0 centimeters.
*Axis diameter*.—Ranging from about 6.6 centimeters to about 7.8 centimeters with an average of about 8.0 centimeters.
*Stem*.—Not Clubbed.
*Stem length*.—Ranging from about 1.5 centimeters to about 2.7 centimeters with an average of about 2.1 centimeters.
*Stem diameter at midpoint*.—Ranging from about 1.5 millimeters to about 2.9 millimeters with an average of about 2.5 millimeters.
*Stem color*.—From the Yellow-Green group (RHS 153B).
*Stem pubescence*.—None.
*Stem cavity shape*.—Mostly acute, some acuminate.
*Stem cavity lipped*.—No.
*Stem cavity russet*.—Small amount at base of cavity. About 10-20% of surface covered.
*Stem cavity russet color*.—From the Greyed-Brown group (RHS N199C).
*Stem cavity width*.—Ranging from about 3.4 centimeters to about 3.8 centimeters with an average of about 3.6 centimeters.
*Stem cavity depth*.—Ranging from about 1.7 centimeters to about 2.2 centimeters with an average of about 2.0 centimeters.
*Basin cavity*.—Smooth surface, not ribbed. Modest crowns, ranging from about 0 to 3.
*Basin cavity shape*.—Considered conical.
*Basin cavity width*.—Ranging from about 3.0 centimeters to about 3.5 centimeters with an average of about 3.2 centimeters.
*Basin cavity depth*.—Ranging from about 1.0 centimeters to about 1.4 centimeters with an average of about 1.3 centimeters.
*Basin cavity eye*.—Considered convergent in shape.
*Basin cavity eye pubescence*.—Light density over about 100% of surface area.
*Basin cavity eye pubescence color*.—From the White group (RHS 155C).
*Skin appearance*.—Mostly flush with occasional small irregular mottling patches.
*Skin color*.—Flush from the Greyed-Yellow group (RHS 160A). Mottling from the Yellow-Green group (RHS 144D).
*Skin thickness*.—Considered thin. About 0.05 millimeters in thickness.
*Skin texture*.—Generally smooth.
*Skin lenticels*.—Generally present and flush to surface.
*Skin lenticels shape*.—Generally round and ranging from about 0.1 millimeters to about 0.2 millimeters in diameter.
*Skin lenticels number*.—About 3 to 4 per square centimeter.
*Skin lenticels color*.—From the White group (RHS 155A), surrounded by a halo of color from the Yellow-Green group (RHS 144D) ranging from about 0.2 millimeters to about 0.3 millimeters.
*Core position*.—Considered median.
*Core line position*.—Considered marginal.
*Core shape*.—Obovate.
*Core length*.—Ranging from about 29.5 millimeters to about 36.1 millimeters with an average of about 32.4 millimeters.
*Core diameter*.—Ranging from about 40.8 millimeters to about 47.3 millimeters with an average of about 43.4 millimeters.
*Cell tufted*.—No
*Cell shape*.—Obovate.

*Cell length*.—Ranging from about 12.0 millimeters to about 17.9 millimeters with an average of about 14.9 millimeters.

*Cell width*.—From about 10.5 millimeters to about 22.8 millimeters with an average of about 11.1 millimeters.

*Cell wall-to-wall width*.—Ranging from about 5.0 millimeters to about 7.3 millimeters with an average of about 5.0 millimeters.

*Tube shape*.—Funnel shaped.

*Tube stamen position*.—Marginal.

*Tube axis*.—Symmetrical and open.

*Seed number*.—From about 2 to 3, mostly 3.

*Seed shape*.—Considered acute.

*Seed length*.—Ranging from about 8.1 millimeters to about 9.2 millimeters with an average of about 8.6 millimeters.

*Seed width*.—Ranging from about 4.2 millimeters to about 4.8 millimeters with an average of about 4.5 millimeters.

*Seed depth* (*wall to wall*).—Ranging from about 2.9 millimeters to about 3.4 millimeters with an average of about 3.1 millimeters.

*Seed color*.—From the Greyed-Orange group (RHS 166A).

*Flesh mouth feel*.—Snappy, crisp, juicy, and melting.

*Flesh color*.—From the White group (RHS 155D).

*Aroma*.—Moderately lite apple aroma.

*Date of harvest maturity*.—Sep. 19, 2019.

*Maturity pressure*.—Ranging from about 17 pounds to about 26 pounds with an average of about 21.1 pounds.

*Maturity starch*.—Rating of 4.0 using the 'Honeycrisp' index.

*Maturity soluble solids*.—Ranging from about 17.0 brix to about 19.2 brix with an average of about 18.3 brix.

*Maturity malic acid*.—About 0.215%

*Keeping quality*.—Excellent. About 9 months in common storage.

*Productivity*.—Moderate to heavy.

*Pollination*.—Any diploid apple of the same bloom season.

*Use*.—Dessert.

*Disease and insect resistance*.—Considered to be susceptible to all insects and diseases found in the region of north-central Washington state.

Although the new variety of apple tree possesses the described characteristics when grown under the ecological conditions prevailing in Brewster, Wash., in the north-central part of Washington state, it should be understood that variations of the usual magnitude and characteristics incident to changes in growing conditions, fertilization, pruning and pest control as well as horticultural management practices are to be expected.

What is claimed is:

1. A new and distinct variety of Apple tree named 'DS 102' as herein illustrated and described.

* * * * *